United States Patent [19]

Gariépy

[11] Patent Number: 5,674,977
[45] Date of Patent: Oct. 7, 1997

[54] BRANCHED SYNTHETIC PEPTIDE CONJUGATE

[75] Inventor: Jean Gariépy, Toronto, Canada

[73] Assignee: The Ontario Cancer Institute, Toronto, Canada

[21] Appl. No.: 257,307

[22] Filed: Jun. 9, 1994

Related U.S. Application Data

[63] Continuation-in-part of Ser. No. 14,180, Feb. 5, 1993, abandoned.

[51] Int. Cl.$^6$ .............................. C07K 4/00; C07K 7/02; C07K 14/00
[52] U.S. Cl. .................. 530/324; 530/327; 530/328; 530/329; 530/330; 530/332; 530/345; 930/290
[58] Field of Search ............................ 530/324, 325, 530/326, 327, 328, 329, 330, 332, 350, 345, 405; 514/12, 13, 14, 15, 16, 17, 18, 492; 544/80; 930/290; 424/1.69, 9.34, 9.411, 179.1, 180.1, 182.1, 194.1, 201.1, 202.1, 203.1

[56] References Cited

U.S. PATENT DOCUMENTS

| | | | |
|---|---|---|---|
| 4,289,872 | 9/1981 | Denkewalter et al. | 528/328 |
| 4,645,661 | 2/1987 | Schonbaum | 424/10 |
| 4,764,504 | 8/1988 | Johnson et al. | 514/12 |
| 5,057,313 | 10/1991 | Shih et al. | 424/85.91 |
| 5,080,898 | 1/1992 | Murphy | 424/94.1 |
| 5,114,713 | 5/1992 | Sinigaglia | 530/806 |
| 5,229,490 | 7/1993 | Tam | 530/409 |
| 5,368,712 | 11/1994 | Tomich et al. | 204/403 |

FOREIGN PATENT DOCUMENTS

| | | |
|---|---|---|
| 0 339 695 | 11/1989 | European Pat. Off. . |
| 3766 | 3/1993 | WIPO . |

OTHER PUBLICATIONS

Roberts and Caserio Basic Principles of Organic Chemistry, 2nd ed. Menlo Park: W.A. Benjamin, Inc, 1977, pp. 1175–1176.
Stryer, L. Biochemistry, 3rd ed. New York: W.H. Freeman and Co. 1988, pp. 19–21.
PNAS, vol. 86, issued Dec. 1989, Tam et al, "Vaccine Engineering Enhancement of Immunogenicity . . . ", pp. 9084–9088.
Tam, Proc. Natl. Acad. Sci. USA, 1988, vol. 85, pp. 5409–5413.
Tung et al., Proc. Natl. Acad. Sci. USA, 1992, vol. 89 (15) 7114–8 (AB).
Lanford et al., Cell, vol. 46 (1986) pp. 575–582.
Dworetzky et al., J. Cell Biol., vol. 107, 1988 pp. 1279–1287.
Roberts et al., Cell, vol. 50 (1987) pp. 465–475.
Goldfarb et al., Nature, vol. 322 No. 14, 1986 pp. 641–644.
Patel, Biochem. Soc. Trans, 1989, 17(5) 931.
McMartin, Biochem. Sci. Trans., 1989, 17(5) 931–934.
Bundgaard et al., Biochem Soc. Trans, 17(5) 1989, 947–949.

*Primary Examiner*—Jeffrey E. Russel
*Attorney, Agent, or Firm*—Ridout & Maybee

[57] ABSTRACT

The invention is a branched synthetic peptide conjugate which can be designed to bind to a target cell surface receptor, to penetrate into target cells, and to deliver a diagnostic probe or cytotoxic functionality to a desired site of action. The invention provides a relatively small molecule of flexible design having a branched structure for systematically incorporating a desired number of cytotoxic functions, peptide-based localization signals or diagnostic probes. The invention addresses problems associated with protein-based therapeutic or diagnostic agents.

7 Claims, 10 Drawing Sheets
(4 of 10 Sheets in Color)

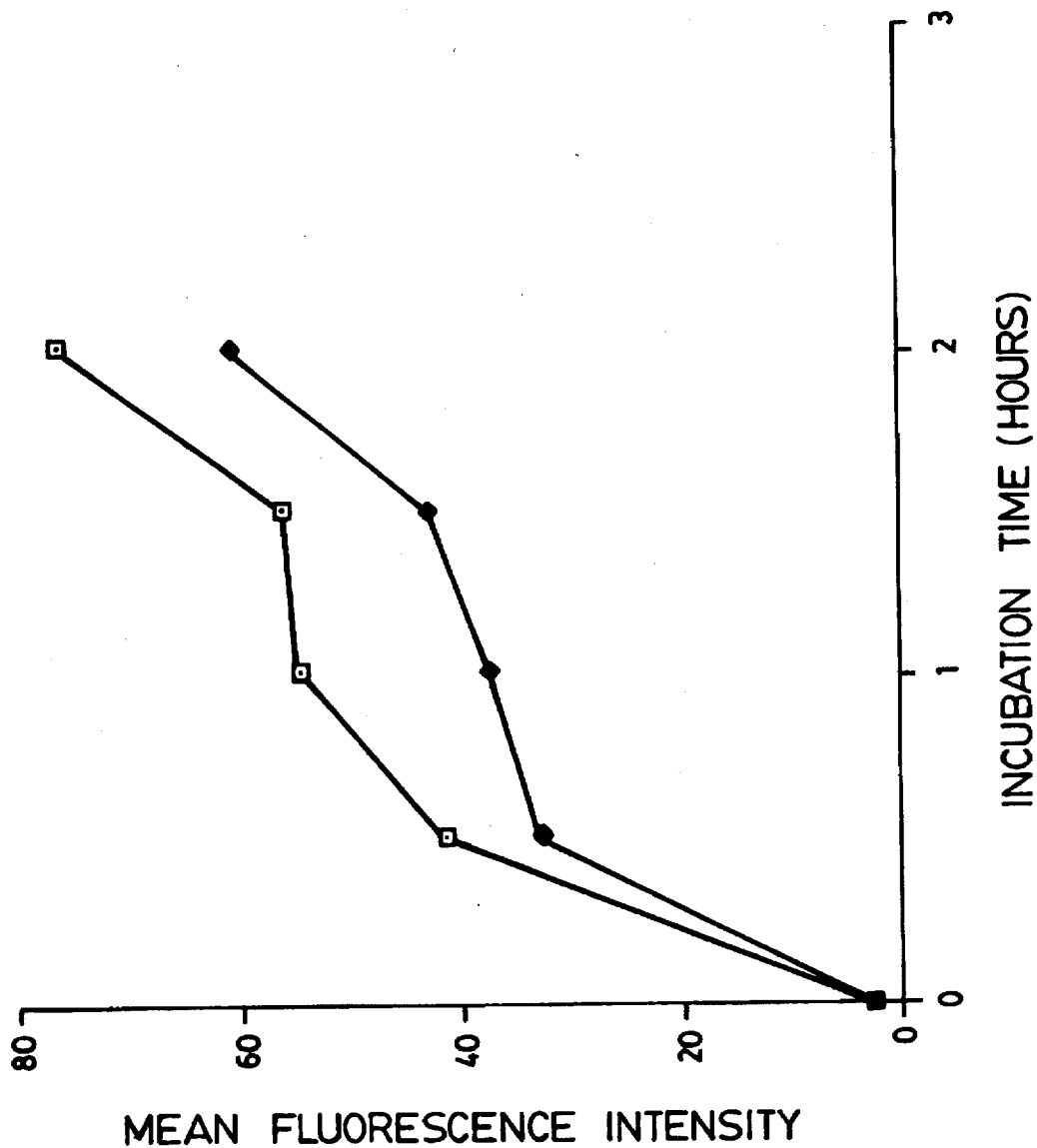

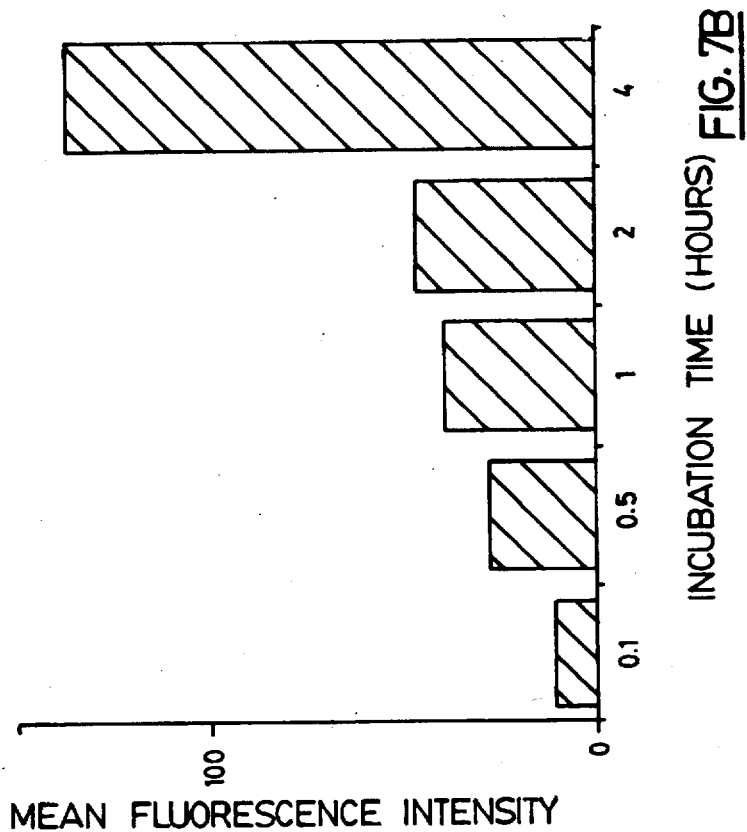
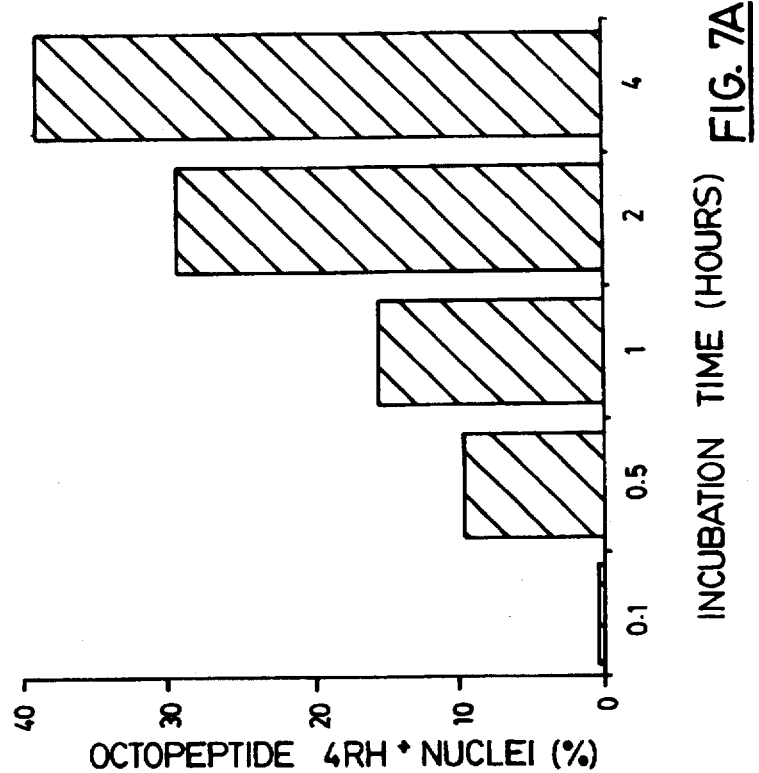

BRANCHED SYNTHETIC PEPTIDE CONJUGATE

This application is a continuation-in-part of Ser. No. 8/014,180 filed Feb. 5, 1993, now abandoned.

The invention is a class of branched synthetic peptide conjugate intracellular vehicles which can bind to a target cell surface receptor and which can penetrate into target cells and deliver a diagnostic probe or a cytotoxic functionality to a desired site of action. The composition of the invention has a plurality of sites for the attachment of diagnostic or cytotoxic groups.

The phenomenon of drug resistance in cancer biology has led to the increasingly rapid development of new generations of therapeutic agents. The design of low molecular weight therapeutics remains mostly based on identifying broad classes of anticancer agents and on screening libraries of related compounds. While the advent of protein-based therapeutics (e.g. radio-immunoconjugates and growth factor-toxin fusion constructs) offers new hopes in specifically targeting and killing cancer cells, their large size and folding complexity have created design problems relating to the immunogenicity and penetration rate of such molecules that have limited their targeting potential and usefulness in clinical trials.

The understanding of mechanisms leading to the endocytosis, vesicular transport and compartmentalization of proteins inside cells has recently been broadened by the discovery of domains in proteins coding for their transport, retention or retrieval into cellular compartments. Cellular events such as retrograde transport and transcytosis have been characterized by the study of bacterial and plant toxins in conjunction with the use of agents such as brefeldin A and cerulenin. Based on this emerging spectrum of molecular and cellular information, an opportunity now exists for designing de novo peptide-based agents that can target selected compartments inside cells. Few systematic approaches presently exist that will allow the design of molecules able to act as intracellular targeting agents. The screening of chemical libraries using functional or receptor binding assays still represents a common, but random, approach for identifying useful low molecular weight compounds. However, molecular candidates able to perform only one cellular task will most likely prove inadequate in carrying out a series of specific cellular functions. Another viable but relatively long term strategy combines the use of mutagenesis and high resolution structural studies directed at finding useful protein variants based on existing protein designs. For example, the bacterial toxin pseudomonas aeruginosa exotoxin A is a protein composed of three defined functional domains coding for cellular uptake, membrane translocation and cytotoxicity. Its study has led to the engineering of hybrid proteins that retain the toxin's cellular functions but have altered receptor-binding properties (Chaudhary et al., 1987; Lorberboum-Galski et al., 1987; Chaudhary et al., 1988; Siegall et al. 1988; Brinkmann et al., 1992; Kreitman et al., 1993). Unfortunately, the dimensions and structural complexity of such constructs establish important constraints exemplified by their possible immunogenicity, their reduced ability to penetrate solid tumours and tissues with altered vasculature, and the lack of flexibility in redesigning simpler constructs. An alternate, but yet untested strategy would be to adopt the minimalist view that domains of proteins or simple polypeptides have already been identified which can code for all necessary transport tasks needed to build prototype intracellular vehicles. A starting requirement is to identify a series of transport tasks and to assemble the required signals onto a flexible scaffold that allows the proper presentation of multiple functional domains. Recent advances in solid-phase peptide synthesis, particularly in the areas of branched peptide technology (Tam, 1988, 1989), and orthogonal synthesis strategies (Field and Noble, 1990), have dramatically broadened the flexibility and ease of creating novel multidomain-containing peptides.

The present invention provides relatively small branched peptides that incorporate targeting features of large proteins, and cytotoxic groups or radionuclides to create peptide-like agents having therapeutic or diagnostic properties. The invention addresses the various requirements for target specific diagnostic or therapeutic agents by providing a modular framework for systematically incorporating a well defined number of cytotoxic functions (e.g., metal chelators, DNA intercalators, alkylating agents), peptide-based localization signals or diagnostic probes (e.g. fluorescent, paramagnetic, ferromagnetic or radioactive groups) or a combination of these. The peptides are branched to provide a plurality of sites for attachment of a desired combination of peptide chains, cytotoxic agents or diagnostic probes. The peptide backbone of a molecule of the invention can be constructed using D-amino acids or peptide-like mimetics in order to resist degradation. Importantly, the peptides of the invention are readily synthesized using standard techniques and may be customized in accordance with the needs of a particular application.

The invention may be described as a series of peptide and chemical domains (D) which may be separated by junctions (J). Each domain performs a particular cell targeting or a cellular function. Junctional segments are spacer regions that may in some cases allow the incorporation of chemically active moieties or markers. These domains and junctions are assembled on a branched polymer (BP) scaffold. The branching of the peptide is preferably provided by a polylysine construct having free α and ε $NH_2$ groups to which linear series of domains and junctions can be attached. A preferred number of branches for the BP unit is 8, and such structures are referred to herein as "octopeptides".

BRIEF DESCRIPTION OF THE DRAWINGS

The file of this patent contains at least one drawing excluding color. Copies of this patent with color drawings will be provided by the Patent and Trademark Office upon request and payment of the necessary fee.

FIG. 6A shows the effects of ATP synthesis inhibitors on octopeptide 4Rh uptake by CHO cells. Cells were incubated at 37° C. in the presence (♦) or absence (□) of $NaN_3$ (5 mM) and 2-deoxyglucose (10 mM).

FIG. 7A is a histogram showing the nuclear uptake of octopeptide 4Rh in CHO cells over time. Ordinate values were determined by flow cytometry.

FIG. 7B is a histogram showing rhodamine mean fluorescence intensities for 4Rh+/7-AAD+ nuclei over time using octopeptide 4Rh.

Figure 1:
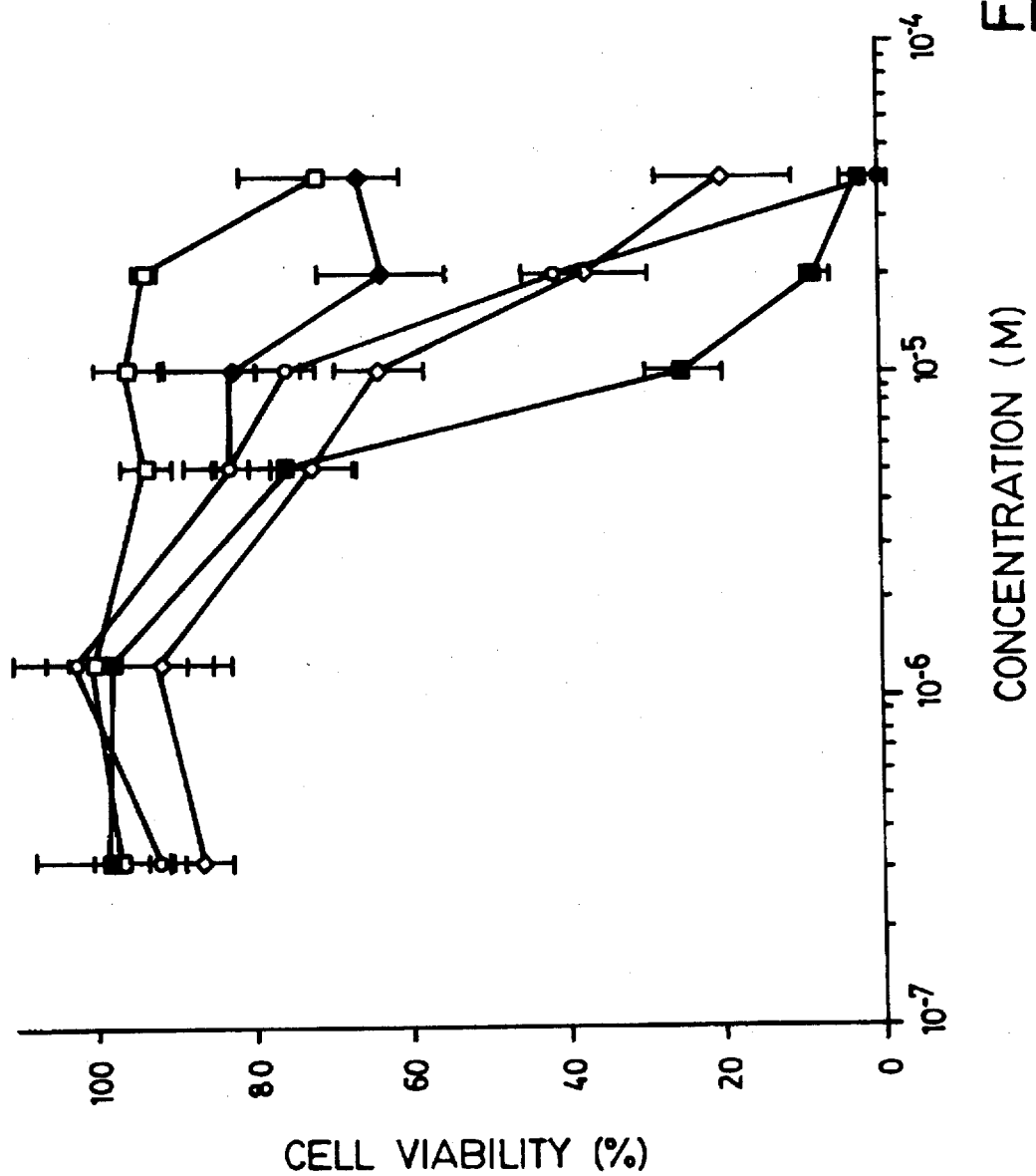
FIG. 1 is a graph showing cytotoxicity of octopeptides towards CHO cells following 20 hr. exposures of cells to various concentrations of octopeptides. Symbols: □, peptide 1; ♦, octopeptide 2; O, octopeptide 3; ◊, octopeptide 4; ■, octopeptide.

While the invention has broad application, it will be described with reference to a preferred embodiment used for the targeting of the cell nucleus. Indeed, the driving force for the creation of branched synthetic peptides of the invention arose from the desire to develop relatively small molecules for carrying chemotherapeutic drugs for delivery to selective sites inside specific cells.

Advances in chemotherapy have lead to new generations of drugs that can cure certain leukemias and lymphomas and prolong the lives of patients with breast, ovarian and other types of cancer. Chemical agents can potentially be designed to be relatively selective for cancerous cells, and thus, less damaging to normal tissues than is possible with therapeutic approaches involving radiation and surgery. Unfortunately, the treatment of cancer patients with cytotoxic drugs often leads to relapse after an initial remission due to the survival and rapid growth of drug-resistant tumor cells. The frequent occurrence of this phenomenon has led to the increasingly rapid development of new generations of chemotherapeutic agents. The identification of low molecular weight chemotherapeutics remains mostly based on the initial discovery of classes of compounds possessing anticancer properties and the subsequent design of analogues with desirable pharmacological properties. The process is frequently iterative and aimed at identifying chemical moieties that are essential for the efficacy of a class of agents. A rapidly expanding class of targeting agents includes all existing protein-based conjugates developed as a result of advances in hybridoma technology and molecular biology. Growth factor-toxin fusion proteins and radioimmuno-conjugates represent just two examples of a growing number of powerful protein-based therapeutic agents. Early clinical trials aimed at evaluating the usefulness of protein-based targeting agents have highlighted problems associated with their immunogenicity and their rate of penetration and residency at tumor sites in relation to healthy tissues. Researchers in this field are now faced with the task of reducing the size and altering the structures of these targeting agents without compromising their selectivity and toxicity. Attempts have been made to use chemically derived IgG fragments or to engineer smaller domains of antibodies. Such approaches have limitations inherent to the complexity of large protein designs.

An objective of the present invention is to exploit the current knowledge of active transport mechanisms to deliver toxic agents into cells in direct competition with detoxification mechanisms arising from selection processes leading to drug resistance. In the past decade, protein signals have been identified that lead to the sorting and compartmentalization of proteins inside cells and organelles. These signals can take the form of small defined sequences of amino acids. Thus, peptide sequences coding for cellular transport functions can be used to construct de novo peptide-based conjugates according to the invention that carry diagnostic or cytotoxic functionalities or both.

The branched peptides of the invention are readily synthesized using existing or modified procedures of classical solid phase peptide synthesis. In addition to being rapid and simple, solid phase peptide synthesis permits the removal of unreacted reagents and by-products at each step of the synthesis. Also, each synthetic step may be repeated until satisfactory yields are obtained.

The peptides of the invention are branched to provide multiple copies of signal sequences and of the cytotoxic/diagnostic probes. The peptides may be customized for various diagnostic and therapeutic applications in association with a wide range of targeting agents. Alternatively, the peptides may include one or more peptide-based or peptide mimic (i.e., a peptide comprising non-naturally occurring amino acids) sequence able to act as a "built-in" targeting agent.

The branched synthetic peptide conjugate of the invention is shown by the general formula I,

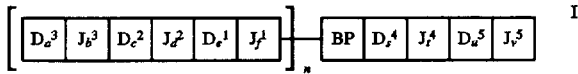

where D is a domain which is a peptide or peptide mimic specific for binding to a target cell surface receptor, or for enabling the transport of the branched synthetic peptide across the plasma membrane of a cell, or for localization into a specific internal cell compartment; a cytotoxic group; or a diagnostic probe;

J is a junctional segment or a carboxy-terminal structural unit which is an amino acid residue or a short peptide;

BP is a branched polymer comprising diamino-carboxylic acid residues which provide the branched synthetic peptide with a plurality of amino-terminal portions;

wherein each of a, b, c, d, e, f, s, t, u, or v may be 0 or 1, and at least two of a, c, e, s and u is 1;

n is an integer ≧ 2; and one of $D^1$, $D^2$ or $D^3$ is present and is a polycationic linear peptide or peptide mimic.

The first step in the construction of a peptide conjugate of the invention is to couple at least one amino acid, and preferably, for most purposes, a short peptide of up to about 10 amino acid residues to a solid support for the purpose of providing a molecular arm for the introduction of a localization signal or the attachment of cytotoxic/diagnostic/reactive moieties. This C-terminal arm of the peptide may comprise units $D_s^4 J_t^4 D_u^5 J_v^5$ of formula I or where all s t, u and v are 0, the C-terminus is provided by the BP unit.

The second part of the peptide conjugate of the invention is a branched polymer (BP) formed from diamino-carboxylic acids such as isomers of lysine, ornithine, 1,2-diaminopropionic acid, and 1,3-diamino-butyric acid. The preferred branch forming amino acid is L-lysine; however, the use of D-lysine and D-amino acids for construction of the branched polymer will reduce the rate of degradation of the peptide in vivo, and the use of shorter diaminocarboxylic acids for branching produce a more compact structure. The branched polymer is connected to the C-terminal arm (when present) via a peptide bond formed between the first diaminocarboxylic acid and the amino group of the last residue of the $D_s^4 J_t^4 D_u^5 J_v^5$ portion When the desired number of amino groups have been assembled onto the branched polymer (BP) of the peptide, the construction of linear N-terminal branches is initiated by the use of non-branching amino acids (using, for example, t-Boc- or Fmoc-Nα protected amino acids with no similar acid or base labile side chain protecting groups) or other molecular spacers. The N-terminal branches of the peptide are composed of units $D_a^3 J_b^3 D_c^2 J_d^2 D_e^1 J_f^1$ of formula I.

In order to develop peptide vehicles able to cross the plasma membrane, the fact that linear chains of polycationic amino acids such as poly(L-lysine) are rapidly internalized by cells and are able to enhance the cytoplasmic transport of macromolecules such as albumin and horseradish peroxidase (Ryser and Shen, 1978; Shen and Ryser, 1978, 1979; Arnold et al., 1979) was exploited. To facilitate the synthesis of peptides carrying a large but defined number of cationic charges, branched peptides were constructed containing a single carboxy-terminal domain and eight amino-terminal arms. These preferred embodiments of the invention are referred herein as octopeptides. The synthesis of branched peptides was developed by Tam and his coworkers (Tam, 1988, 1989; Tam and Lu, 1989) in their attempts to design peptide-based vaccines. In the present invention, by introducing the linear peptide KKKKK (SEQ ID NO:2) on each arm (referred to as the cytoplasmic translocation signal or CTS), a defined branched polylysine domain of 5 kDa (40 lysine residues) could be created without resorting to a long synthetic scheme. Clearly, the length of this linear polycationic peptide may vary, and other amino acids may be used (e.g. ornithine).

In order to carry this peptide vehicle to the nucleus of cells, model octopeptides were synthesized to include the well characterized nuclear localization signal (NLS) of the SV40 large T antigen (Kalderon et al., 1984). This NLS sequence has been shown to cause the localization of non-nuclear proteins such as bovine serum albumin and immunoglobulin G at and into the nucleus of frog oocytes or mammalian cells following their microinjection into the cytoplasm (Goldfarb et al., 1986; Lanford et al., 1986). Studies based on the use of this sequence in constructing NLS-protein conjugates have shown that the efficiency of nuclear targeting rose as the number of peptides coupled to the reporter protein was increased (Roberts et al., 1987; Dworetzky et al., 1988). High numbers of coupled NLS sequences were required for efficient binding and subsequent ATP-dependent nuclear uptake, suggesting that multivalent interactions between the signals and intracellular receptors might increase the efficiency of protein import (Newmeyer and Forbes, 1988). The branched peptide design of the invention represents a synthetic geometry well suited to the introduction of multiple copies of the SV40 NLS sequence into each octopeptide. Accordingly, the sequence TPPKKKRKVEDP (SEQ ID NO:1) spanning residues 124 to 135 of the SV40 large T antigen was incorporated into each of the eight N-terminal branches of octopeptides 3, 4, 4Rh, 5 and 5Rh. Finally, the DNA intercalator acridine (Acr) was selected for integration into these octopeptides in view of its appropriate fluorescence properties which allowed for the monitoring of the migration of peptides inside cells by fluorescence microscopy. The incorporation of a rhodamine (Rh) probe at the C-terminal end of octopeptides 4Rh and 5Rh was used to detect octopeptides during transport studies using flow cytometry. In order to test the usefulness of each domain, peptide 1 (Acr-NLS-CTS) and octopeptides 2 and 3 were synthesized so as to lack one domain (branched polymer, CTS or NLS signals). Octopeptides 4Rh, 5 and 5Rh contained all three of these domains.

Using the nomenclature of formula I, octopeptides 2, 3, 4 and 5 were prepared having some or all of the components of the formula II:

$$[D^3D^2D^1J^1]_8—BP J^4 \qquad II$$

where $J^1$ is Gly-Gly, $J^4$ is Tyr-Gly-βAla, $D^1$ is CTS, $D^2$ is NLS, $D^3$ is Acr, and BP is $(Lys)_4(Lys)_2Lys$ having a branched structure with 8N-terminals and one C-terminus.

Thus, octopeptides 2, 3 and 4 have the following formulas:

$[D^3D^2J^1]_8—BPJ^4$
octopeptide 2

$[D^3D^1J^1]_8—BPJ^4$
octopeptide 3

$[D^3D^1J^1]_8—BPJ^4$
octopeptide 4

Octopeptide 5 is represented by formula II and has the following structure:

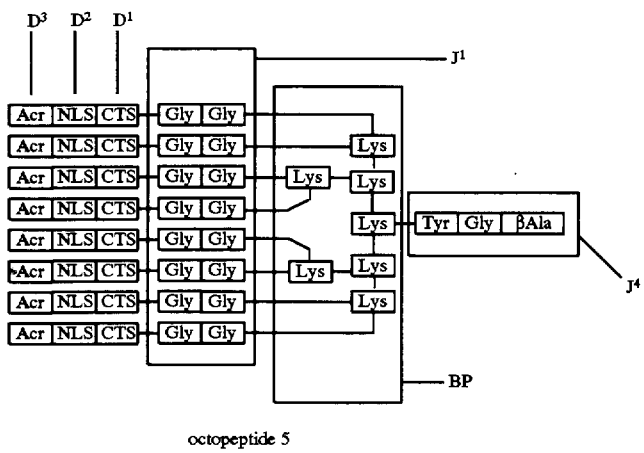

octopeptide 5

By coupling rhodamine to the carboxy end of octopeptides 4 and 5, octopeptides 4Rh and 5Rh were obtained.

The following is a typical synthetic scheme for the preparation of a synthetic peptide conjugate of the invention.
Preparation of octopeptide 5

Octopeptide 5 is a branched peptide containing the DNA intercalator acridine (Acr) that is able to cross the cytoplasmic membrane of cells and accumulate in the cell nucleus. Octopeptide 5 is composed of eight N-terminal branches and one C-terminal arm. The branches are identical and composed of a linear arrangement of three domains; the DNA intercalator agent acridine (Acr; $D^3$), a 12-amino acid sequence of the SV40 large T antigen that is responsible for the nuclear translocation of this protein (NLS; nuclear localization signal; $D^2$) and a 5-residue linear lysine repeat (CTS, cytoplasm translocation signal; $D^1$). These branches are linked to a branched polymer (BP) via a junctional segment ($J^1$) composed of two glycine residues. BP is created after three successive couplings of L-lysine during solid-phase peptide synthesis. The efficiency of the peptide to cross the cytoplasmic membrane is dependent on the level of cationic charges present on the peptide. The presence of 8 branches carrying the CTS repeat dramatically augments the rate of entry of the branched peptide into cells when compared to an individual branch (i.e., peptide 1). The C-terminal arm ($J^4$) is composed of three residues used in the analytical evaluation of the construct; tyrosine can be radiolabeled and its absorbance measured at 280 nm, glycine and β-alanine are amino acid standards to monitor the concentration and amino acid composition of the construct.

Octopeptide 5 was prepared by solid phase peptide synthesis on an automated Applied Biosystems model 430A Peptide Synthesizer using t-Boc protected amino acids and PAM (phenylacetamidomethyl) resin supports. A similar octopeptide can be generated using Fmoc amino acids and acid sensitive resin supports. Unless indicated, all coupling steps were carried out for 1 to 2 hours at room temperature using symmetric anhydride derivatives of protected amino acids dissolved in dimethylformamide. Each coupling step was then repeated in 10% (v/v) hexafluoroisopropanol in dichloromethane. In the case of arginine and glutamine derivatives, HOBt esters were prepared in dimethylformamide and the coupling step carried out in the same solvent. All synthesis protocols employed were those established by the manufacturer (Applied Biosystems, Foster City, Calif.). Each coupling step was monitored by the quantitative determination of free amino groups present on the resin (quantitative ninhydrin test). Typically, the efficiency of each coupling step was greater than 99%. The first residue coupled to the PAM resin was β-alanine (β-aminopropionic acid) and the substitution on the resin support was 0.1 mmole/gram of resin. The initial low substitution value on the resin insures that crowding on the resin with peptide chains will not occur as a result of three branching steps (i.e., maximal substitution of $2^3 \times 0.1$ mmole=0.8 mmole/gram of resin). The β-alanine serves as an internal standard. The second and third residues were glycine and tyrosine respectively and constitute with β-alanine, an analytical spacer arm that permits one to assess the quality of the synthesis (post-synthesis amino acid analysis) and the concentration of the polymer (tyrosine side chain absorbs strongly at 280 nm and can be readily radiolabeled with iodine isotopes) in solution. The fourth residue was Nα(Boc),Nε(Boc)-lysine, an amino acid having its amino groups at the Cα and Cε positions protected with acid labile Boc protecting groups. After deprotecting these sites with TFA, branching is initiated by coupling two equivalents of Nα(Boc),Nε(Boc)-lysine to the two available amino positions. After another round of acid deprotection, the branching step was repeated with this time four amino sites available for coupling. Nα(Boc),Nε(Boc)-lysine was coupled again. The Boc groups on the completed BP domain were deprotected with TFA to expose 8 free amino groups thus allowing the construction of 8 N-terminal arms (n=8). Two glycine(Boc) residues were successively coupled again to act as a spacer ($J^1$) before introducing five consecutive Nα(Boc),Nε(2-Cl-Z)-L-lysine groups. These 5 lysine residues (SEQ ID NO:2) constitute a domain ($D^1$) called the cytoplasm translocation signal or CTS. The presence of 8 of these CTS domains in octopeptide 5 results in a final molecule with a high level of cationic charges and a potential for this octopeptide to be rapidly internalized by cells. The following 12-amino acid sequence (domain $D^2$) was then introduced; Thr-Pro-Pro-Lys-Lys-Lys-Arg-Lys-Val-Glu-Asp-Pro (SEQ ID NO:1). This sequence represents a nuclear localization signal or NLS (residues 124 to 135) for the protein known as the SV40 large T antigen. The NLS antigen was added to each branch in a stepwise fashion with each amino acid in this sequence being coupled one at the time to the growing peptide chain starting with proline-135 (the synthesis is proceeding from the C-terminus to the N-terminus). As the name suggests, the presence of the NLS domain ($D^2$) allows octopeptide 5 to be selectively transported to the nucleus of cells. Although 8 NLS domains are present in this octopeptide construct, a single NLS domain should be sufficient to target this molecule to the nucleus of cells. Junctional segments J² and J³ are absent in octopeptide 5. The final domain introduced in octopeptide 5 is the acridine moiety (D³). The Boc group of threonine-124 was removed in TFA to expose its Nα amino group. The peptide-resin was resuspended in 9-phenoxyacridine dissolved in hot dried/recrystallized phenol and the resulting slurry was mixed with a stirring bar at 80° C. for 16 hours. This coupling step typically exceeded 98% coupling efficiency as determined by ninhydrin analysis of residual free amino groups on the resin. Finally, octopeptide 5 was detached from the support by exposing the peptide-resin to anisole:dimethylsulfide:anhydrous hydrogen fluoride (1:1:10) for 90 minutes at -5° C. The resin was extracted with several ether washes to remove anisole, dimethylsulfide and cleaved protecting groups. The branched peptide was then recovered by extracting the resin with 50% (v/v) acetic acid and lyophilized.

The skilled person will appreciate that the number of N-terminal amino groups can be increased readily to 16 or more, with the upper limit depending on the ability to resolve problems of low coupling rates associated with the crowding of the resin support and the accessibility of free amino groups. The rapidity of the synthesis strategy and its potential for automation represent major advantages in developing the technology. With an expected molecular weight of 17,878 daltons, octopeptide 5 was desalted on a Sephadex G-25 column equilibrated in distilled water to remove low molecular weight impurities resulting from the cleavage step. The recovered octopeptide 5 has 8 (±1) acridine groups and the correct amino acid composition.

The peptide 1 and octopeptides 2, 3 and 4 were prepared in a similar fashion. Octopeptides 4Rh and 5Rh were prepared by adding 0.1 mg of tetramethyl rhodamine-5-(and 6)-maleimide to 1 mg of octopeptide in 0.1M citrate buffer, pH 6.5. After 4 hrs. at 4° C. in the dark, excess rhodamine was removed by size exclusion chromatography on Sephadex G-25 equilibrated in PBS. The compositions of octopeptides 4Rh and 5Rh were confirmed by amino acid analysis.

Cytotoxic properties of peptide constructs

The cytotoxicity of peptide 1 and octopeptides 2-5 was established in Chinese hamster ovary (CHO) cells in order to select a minimal octopeptide concentration suitable for detecting the constructs by flow cytometry and fluorescence microscopy on live cells. The cytotoxicity of each construct was established using the MTT cell viability assay (FIG. 1; Mosmann, 1983). Peptide 1 and octopeptide 2 were not toxic to CHO cells at concentrations as high as 100 µM following a 2 hour incubation period while octopeptides 3 to 5 proved to be cytotoxic at lower concentrations with $CD_{50}$ values ranging from 7 to 30 µM. The data suggests that the branched polylysine matrix (the combination of a branched polymer and CTS domains; octopeptides 3 to 5) dictates the cytotoxicity of the octopeptides. Polylysine has been shown to be cytotoxic to cells, a function which is strongly dependent on its molecular weight. Linear polymers having a mass of less than 13 kDa were shown not to be cytotoxic to HeLa cells (Arnold et al., 1979). In the context of octopeptides, the eight CTS domains amount to a mass of only 5 kDa, suggesting that the tentacular geometry may represent a more cytotoxic presentation of polylysine chains. At a concentration of 1 µM, none of the octopeptides were cytotoxic to CHO cells (FIG. 1). Exposure of CHO cells to octopeptides for periods of time ranging from 2 to 20 hours did not result in significant differences in cell survival. The penetration and localization of acridine and rhodamine chromophores in viable CHO cells were observed during fluorescence microscopy and flow cytometry experiments by exposing cells to concentrations of octopeptides ranging from 0.1 to 1 µM.

Visualization of octopeptide internalization and nuclear localization

Figure 2A:
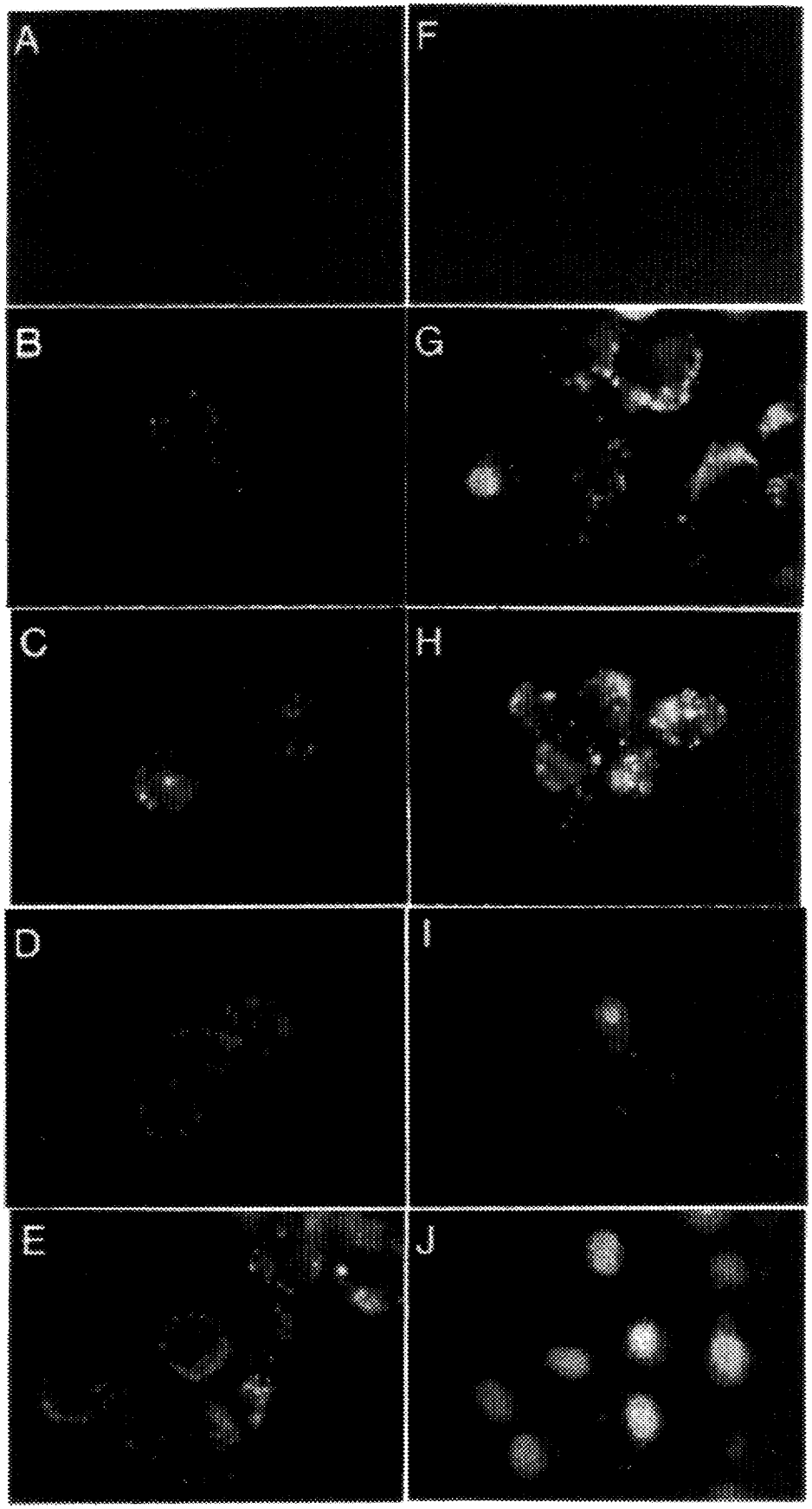
FIG. 2A are fluorescence microphotographs showing penetration and localization of peptide 1 and octopeptides inside live CHO cells by fluorescent markers acridine or rhodamine. The efficiency of cytoplasmic translocation signals (CTS) is illustrated after one hour exposures of CHO cells to peptide 1, octopeptides 2, 3, 4Rh and 5 in panels A–E respectively. Nuclear localization of these compounds after 4 hours is shown in panels F–J respectively.
Figure 2B:
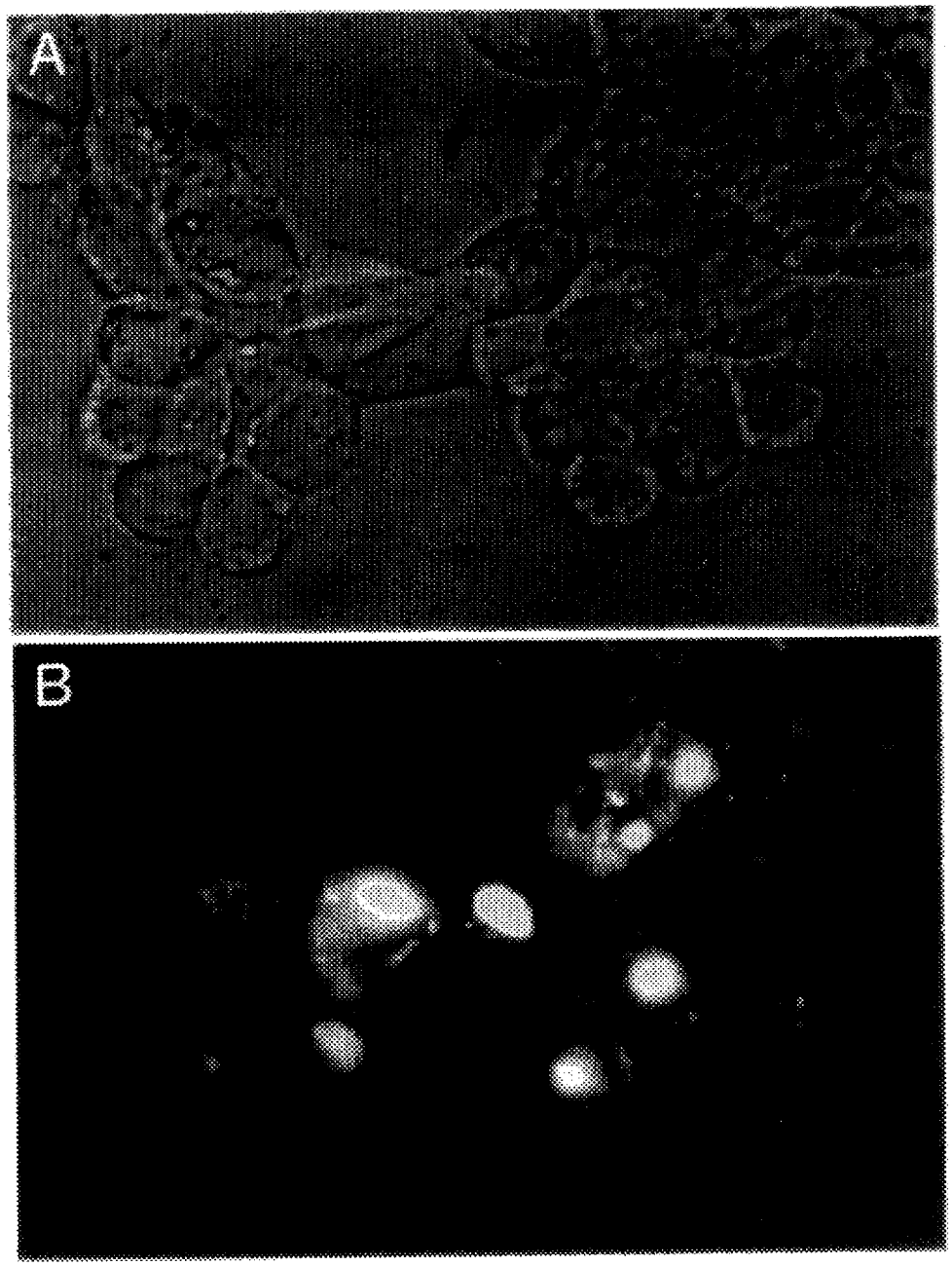
FIG. 2B shows microphotographs of CHO cells labelled with octopeptide 5 after 4 hrs. incubation at 37° C. under visible light (panel A) and under UV fluorescence (panel B).
Figure 3:
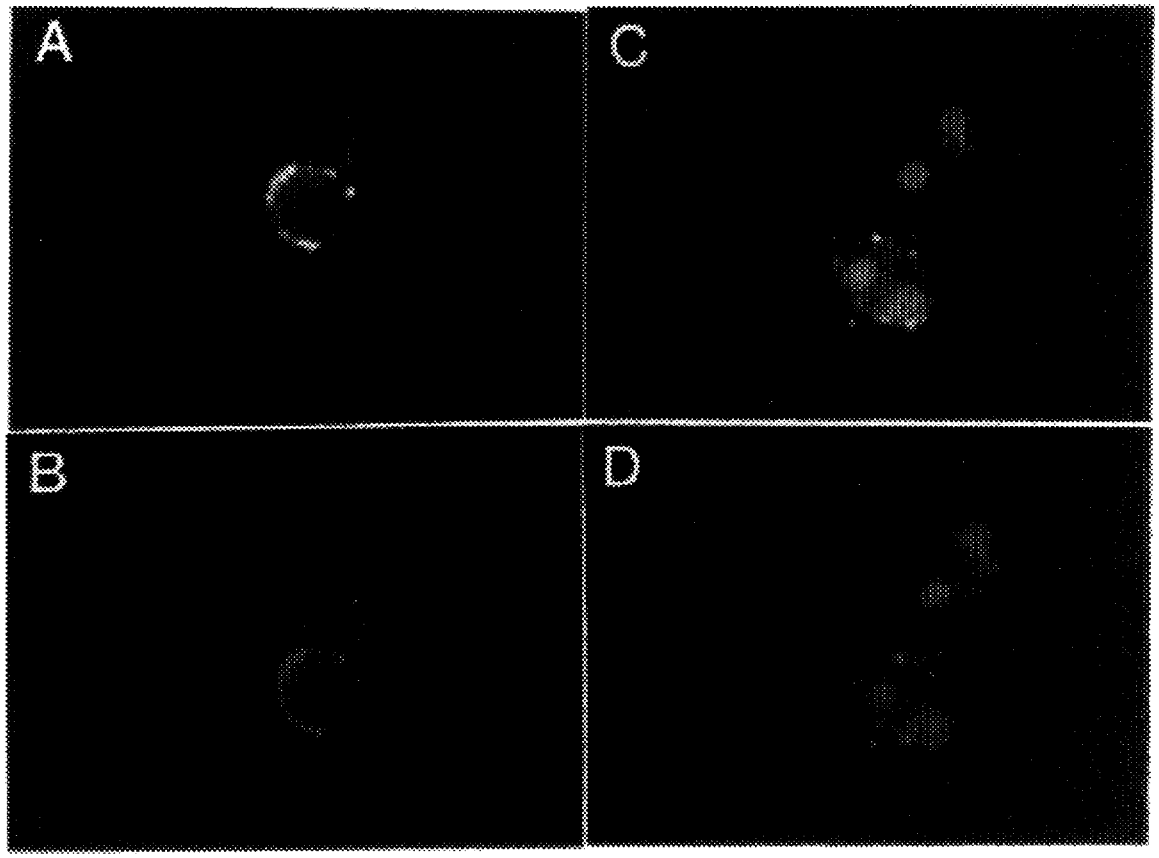
FIG. 3 are microphotographs of CHO cells incubated with octopeptide 5Rh at 4° C. (panels A–Acr fluorescence, and B–Rh fluorescence) and at 37° C. (panels C and D).

The incorporation of acridine and rhodamine into peptide constructs enables the monitoring of their interaction and penetration into CHO cells by fluorescence microscopy. Within the first hour of incubation, octopeptides 3, 4Rh and 5 (FIG. 2A, panels C, D, E) were rapidly internalized by CHO cells in comparison to peptide 1 (no internalization; FIG. 2A, panel A) and octopeptide 2 (FIG. 2A, panel B), confirming the importance of the CTS and BP domains. After 4 hours, all octopeptides (FIG. 2A, panels G to J) had entered cells with only the ones containing NLS domains (4Rh, 5 and 5Rh; FIGS. 2A, panels I, J; FIGS. 3C, 3D) localizing to the nucleus of CHO cells. In the case of octopeptide 3 (FIG. 2A, panel H), the acridine fluorescence was randomly distributed between cytoplasmic and nuclear compartments in agreement with the observation that low molecular weight compounds of less than 60 kDa can passively diffuse through the nuclear pore complexes while the nuclear translocation of NLS-bearing small molecules is regulated by an active transport mechanism (Breeuwer and Goldfarb, 1990). Octopeptide 2 did localize to the nucleus of some cells when CHO cells were exposed to this octopeptide for longer periods of time (up to 18 hours). Octopeptides 4Rh and 5 combining CTS and NLS domains were the most efficiently transported constructs. FIG. 2B illustrates the recurrent observation that octopeptide 5 (as well as 4Rh and 5Rh) typically accumulates in the nucleus of a fraction of CHO cells. Extending the exposure of cells to these octopeptides for up to 18 hours did not result in an overall increase in the number of CHO cells showing nuclear uptake of our constructs. One explanation for this phenomena may be that nuclear import of proteins may be tightly regulated by cell cycle controls as demonstrated for the yeast transcription factor SW15 (Moll et al., 1991) and the SV40 large T antigen (Jans et al., 1991). In addition, it was observed that CHO cells grown in suspension and in monolayers were equally competent in internalizing octopeptides but differ dramatically in terms of their nuclear uptake of the constructs. Nuclear localization of octopeptides was rarely or never observed in confluent monolayers of CHO cells.

Following their cell-surface association and internalization by CHO cells, it remains unclear if octopeptides are degraded as a result of being potentially routed to endosomal or lysosomal compartments. Methotrexate-polylysine conjugates for example have been shown to be degraded in lysosomes (Ryser et al. 1988). Based on the localization behaviour of octopeptide 3 (FIG. 2A, panel H) in relation to octopeptides 4Rh and 5 (FIG. 2A, panels I, J), it can be concluded that the acridine and rhodamine chromophores only accumulate in the nucleus of cells in association with NLS domains rather than as a result of excessive peptide degradation. Preliminary results indicate that octopeptide 5 reconstructed with D-amino acids behaves identically to octopeptide 3 indicating that NLS domains are non-functional when synthesized with D-amino acids (data not shown). If octopeptide 5 is reconstructed with D-amino acids with the exception of the NLS domains (which were maintained as L-amino acids), the resulting analog accumulated in the nucleus of CHO cells in a similar time fashion as octopeptides 4Rh, 5 and 5Rh (data not shown). Thus, the design of protease-resistant constructs did not result in any dramatic differences in localization behavior or signal intensity. Octopeptide 5Rh was designed so that rhodamine and acridine chromophores were located at opposite ends of the lysine-rich (and putative protease-sensitive) NLS and CTS domains. Degradation of this peptide would yield a tetramethyl rhodamine ester derivative which does not accumulate in the nucleus of cells. In fact, tetramethyl rhodamine derivatives are typically used to visualize mitochondrial membrane potential (Ehrenberg et al., 1988; Farkas et al., 1989). Since extensive proteolysis would result in the release of short acridine- and rhodamine-containing peptides lacking intact NLS domains, their co-localization in the nucleus of cells would not be expected (as exemplified by octopeptide 3). In FIGS. 3C and 3D, one observes that both signals accumulate in the nucleus of cells suggesting that the octopeptide 5Rh is only partially degraded in intracellular transport with the consequence that some NLS sequences are still able to guide their nuclear localization. The fact that octopeptides are not necessarily inactivated by a single proteolytic event may represent an important therapeutic advantage.

Membrane association and endocytosis of octopeptides

Figure 4A:
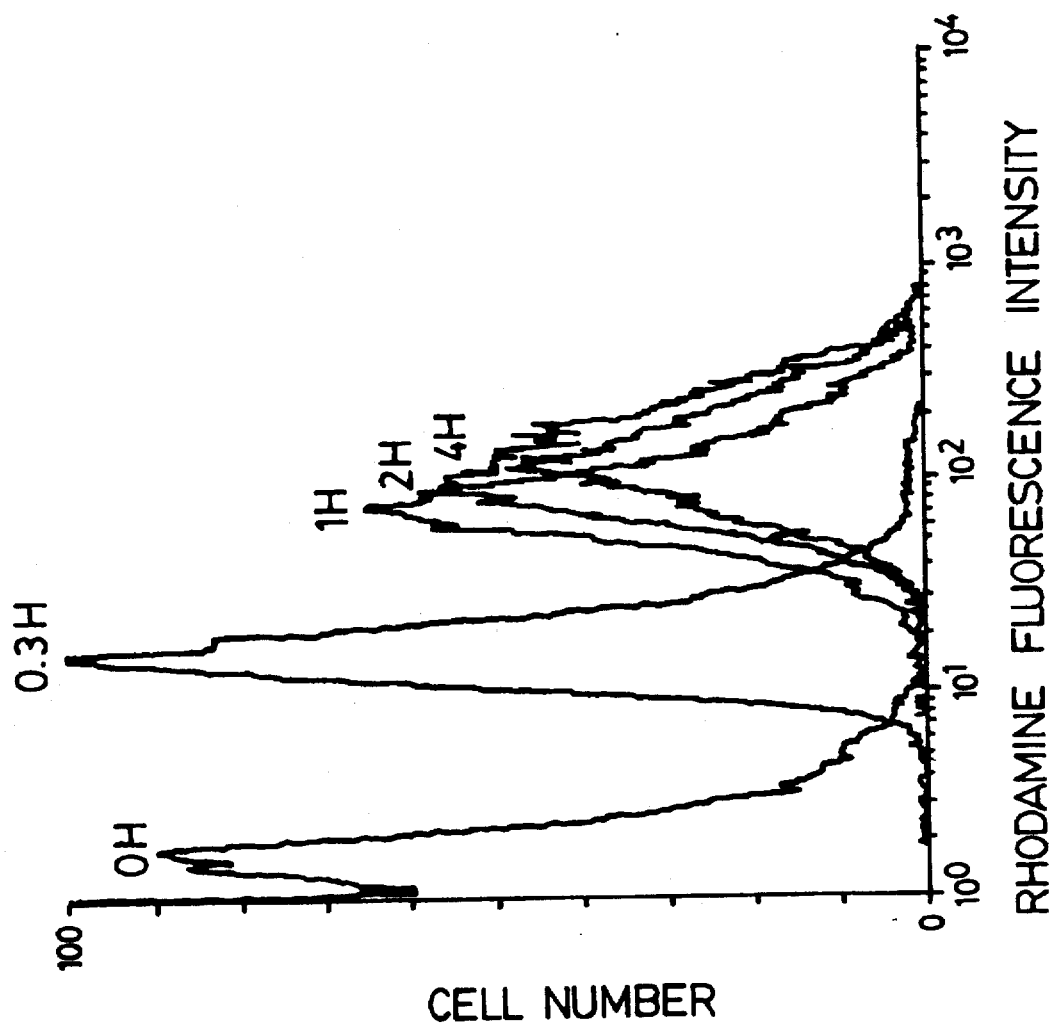
FIG. 4A shows superimposed cytometric histograms illustrating the uptake of octopeptide 4Rh by CHO cells at 37° C. after incubation for 0, 0.3, 1, 2 and 4 hr. respectively.
Figure 4B:
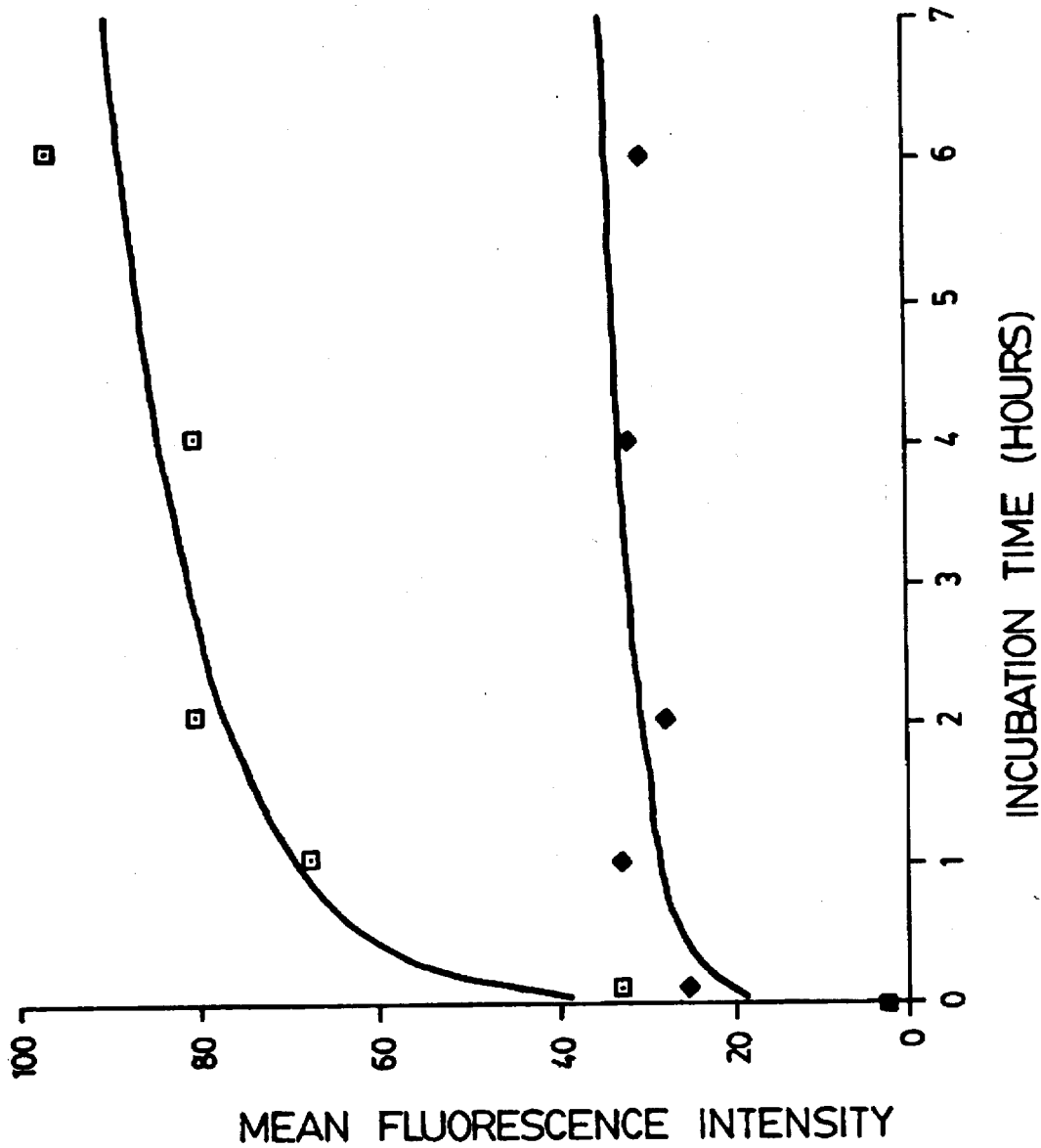
FIG. 4B shows the mean fluorescence intensities observed for $10^4$ cells plotted as a function of incubation time with octopeptide 4Rh. Symbols: ♦, 4° C.; □, 37° C.
Figure 5:
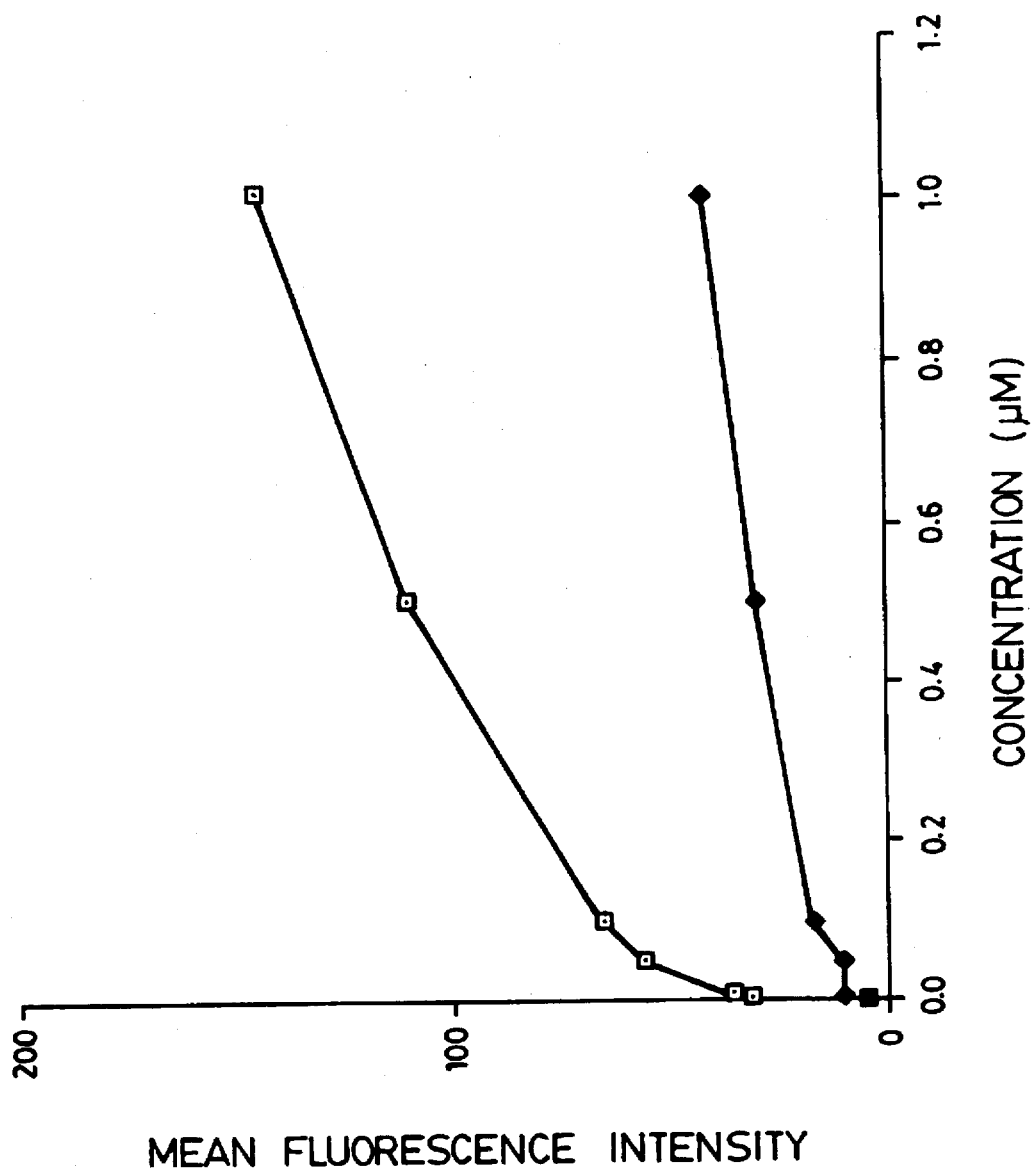
FIG. 5 shows the effects of octopeptide 4Rh concentration on peptide uptake by CHO cells at incubation temperatures of 4° or 37° C. Symbols: ♦, 4° C.; □, 37° C.
Figure 6B:
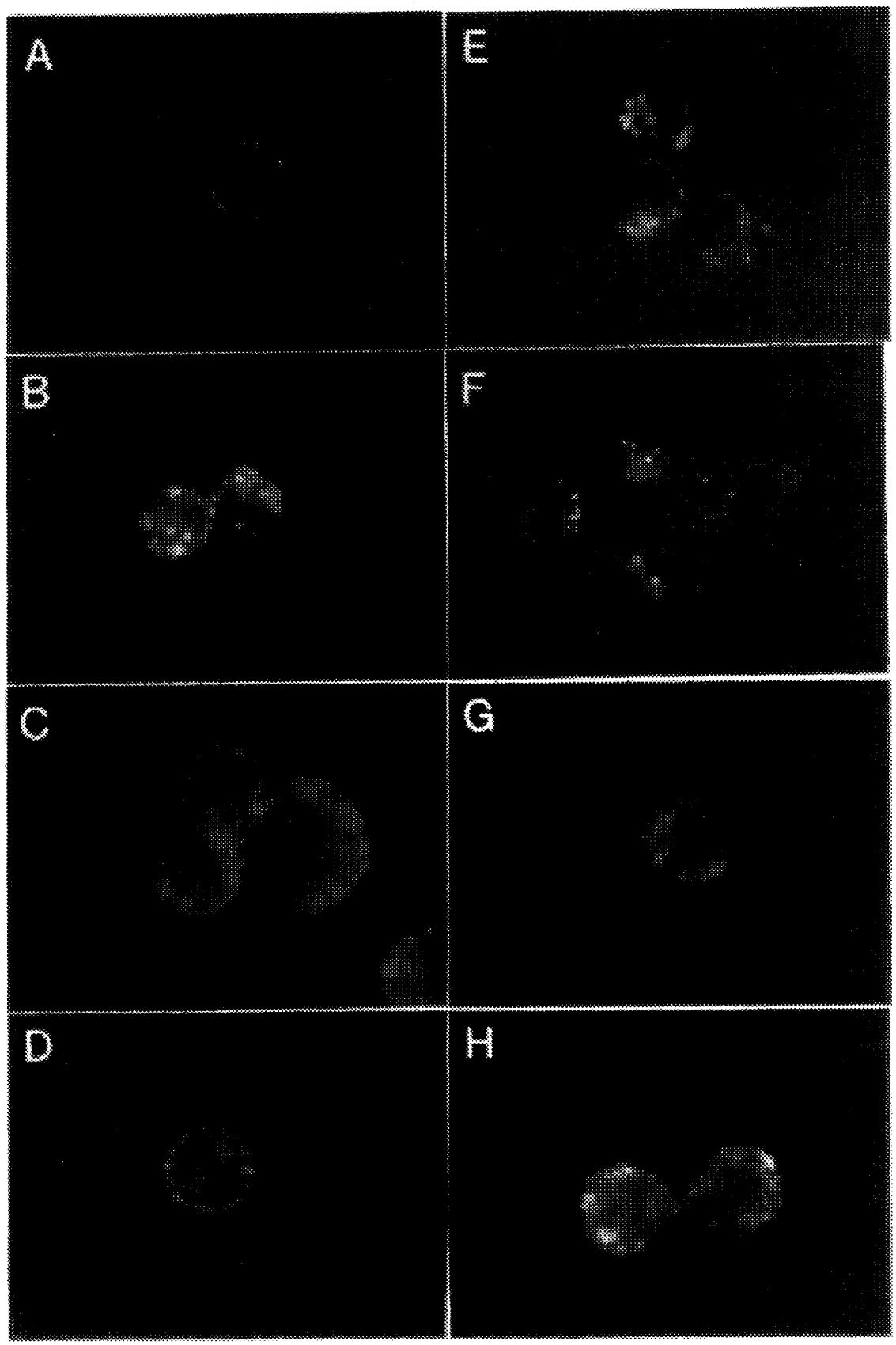
FIG. 6B are fluorescence microphotographs of CHO cells incubated with octopeptides 2, 3, 4Rh and 5 in the presence of ATP inhibitors $NaN_3$ and 2-deoxyglucose, where panels A–D show incubation of the respective octopeptides after 1 hour and panels E–H after 4 hours.

Attempts were originally made to use acridine-containing peptides in flow cytometry experiments. However, the available laser excitation lines did not produce strong emission signals for this chromophore during preliminary analyses. Since octopeptide 4Rh contains a single rhodamine probe as well as both CTS and NLS domains, it represented an analog more suited to the analysis of cellular events by flow cytometry. As discussed above, it was observed that octopeptide 5Rh only associated with the cytoplasmic membrane at 4° C. (FIGS. 3A, 3B). Similarly, exposing CHO cells at 4° C. to all octopeptides resulted in the accumulation of fluorescence signal at the perimeter of the cytoplasmic membrane (results not shown). Using flow cytometry, it was established that in less than one hour, all CHO cells were labelled with octopeptide 4Rh (FIG. 4A; 37° C.). A gradual increase in the mean fluorescence signal of the cell population was observed as a function of time. Monitoring the mean fluorescence intensity of CHO cells exposed to 4Rh at both 4° C. and 37° C. confirmed that peptide-membrane association and peptide import were two distinct steps (FIG. 4B). The fact that both events reached a plateau at later incubation periods could be rationalized by one of two possible import mechanisms: receptor-mediated endocytosis or by the broader but less specific mechanism of adsorptive endocytosis. The existence of a distinct class of receptors for octopeptide 4Rh can only be confirmed if one can demonstrate the saturability and reversibility of the interaction between 4Rh and such receptors. Monitoring the mean fluorescence signal of 4Rh upon addition of increasing concentrations of the octopeptide to CHO cells at both 4° C. and 37° C. suggested that both binding and uptake events are potentially saturable (FIG. 5). However, the addition of excess octopeptide 4 (non-fluorescent analog), to block or displace 4Rh bound to CHO cells at 4° C. did not inhibit its association with these cells (results not shown). These results suggest the existence of low affinity/high occupancy sites for 4Rh on CHO cells reminiscent of a nonspecific uptake process. It is well known that poly-L-lysine associates with the negatively charged surface of mammalian cells and is internalized by a process termed nonspecific adsorptive endocytosis (Ryser and Shen, 1978; Shen and Ryser, 1979; Leonetti et al., 1990). Interestingly, members of the integrin family of cell adhesion molecules, particularly $\alpha_3\beta_1$, $\alpha_5\beta_1$ and $\alpha_6\beta_1$ could serve as a transitory class of cell surface receptors for CTS domains (Vogel et al., 1993). Past studies have shown that inhibitors of ATP synthesis, such as 2-deoxyglucose (10 mM) and sodium azide (5 mM) could inhibit the uptake process of poly-lysine polymers (Leonetti et al., 1990). A weak, but reproducible, inhibition of octopeptides endocytosis into CHO cells in the presence of these reagents was observed (FIG. 6A). No nuclear localization was observed over that time period (FIG. 6B).

Octopeptide uptake into the nucleus

The nuclear import of octopeptides by CHO cells was first visualized by fluorescence microscopy (FIG. 2). The time dependency of this localization process was analyzed by pulsing cells with octopeptide 4Rh for increasing time periods. Exposed cells were typically separated from peptide-containing medium by centrifugation. Cell pellets were washed and their nuclei recovered rapidly by a series of membrane disruption and centrifugation steps. The recovered nuclei were then stained with the fluorescent DNA intercalator 7-AAD. The ratio of 7-AAD+/4Rh+ nuclei in relation to the total number of 7-AAD+ nuclei was determined by flow cytometry. Such an analysis is presented in FIG. 7A and highlights the fact that up to 40% of CHO cell nuclei internalize the octopeptide after a 4-hour period. Nuclear uptake is gradual within the first 4 hours and a lengthening of the 4Rh incubation period does not result in a higher ratio of stained nuclei. It has already been established that endocytosis of octopeptide 4Rh in CHO cells is complete after the first hour of exposure (FIGS. 2 and 4). Thus, there is a short time lag (minutes to hours) between endocytosis and nuclear uptake. Interestingly, the level of nuclear uptake (mean fluorescence intensities; FIG. 7B) could be characterized as a two stage event. One initially observed the staining of the nuclear envelope at early time points (up to 2 hours of incubation) followed by the accumulation of fluorescence signals inside the nuclear compartment (at 4 hours). Nuclear localization of proteins is an ATP-dependent process (Richardson et al., 1988; Newmeyer and Forbes, 1988) which explains why the labelling of the nuclear compartment in the presence of sodium azide and 2-deoxyglucose was not observed (FIG. 6B).

Design and potential applications of octopeptides

A prototypic class of peptides has been designed and synthesized which perform the expected tasks of crossing the cytoplasmic membrane and accumulating in the nucleus of mammalian cells. The initial stage of internalization involves a peptide-membrane association step which probably accentuates the efficiency of the import mechanism through a process of adsorptive endocytosis. Endocytosis may require energy in the form of ATP although the evidence remains limited. The vesicular transport of constructs of the invention must still be analyzed. Protease degradation of these peptide constructs is at best partial (FIGS. 2 and 3), and a significant amount of octopeptide appears to reach the cytoplasm. The process of nuclear uptake is relatively rapid and efficient as demonstrated by flow cytometry (FIG. 7).

EXPERIMENTAL PROCEDURES

Cell line and culture conditions

The Chinese hamster ovary cell subclone AUXB1 (Stanners et al., 1971), was grown routinely in suspension culture at 37° C. in growth medium consisting of $\alpha$-MEM supplemented with 10% FBS and 1 mM glutamine.

Cytotoxicity assay

The quantitative MTT colorimetric assay developed by Mosmann (1983) was used to determine the toxicity of peptide constructs of the invention toward CHO cells. Briefly, CHO cells ($10^4$ cells) suspended in $\alpha$-MEM containing 10% FBS and 1 mM glutamine were seeded in 96-well plates and grown overnight at 37° C. in a humidified 5% $CO_2$ incubator. Increasing concentrations of each peptide were added to cell monolayers and the incubation continued for 20 hours. The peptide-containing medium was replaced with 200 µL of fresh medium containing 0.5 mg/mL MTT. The cells were incubated for 4 hours at 37° C. and subsequently solubilized by adding 50 μL of a 10% (w/v) SDS solution prepared in 0.01N HCl to each well. The blue MTT formazan product generated by living cells was quantified by measuring the optical density of the cellular extract at 620 nm. Exposing CHO cells to peptides for a longer period of time (24–72 hours) did not result in increased cytotoxicity levels at lower doses of peptides. Absorbance values were translated into measurements of cell viability and reflect the average of experiments performed in triplicate.

Fluorescence microscopy

CHO cells ($10^6$ cells) were exposed to a 1 μM solution of either peptide 1 or octopeptides prepared in α-MEM medium. At selected time periods, a sample of each cell preparation was recovered by centrifugation and resuspended in fresh medium. Typically, a drop of unfixed cells was deposited directly on a microscope slide and the fluorescence signal recorded on a Nikon Optiphot fluorescence microscope (magnification:×1000). A standard excitation filter used for monitoring fluorescein chromophores was satisfactory for observing the acridine signal. The rhodamine signal from octopeptides 4Rh and 5Rh was recorded by incubating CHO cells with 0.1 μM of these constructs.

Flow cytometry

CHO cells ($10^6$ cells/ml) were exposed to a 0.1 μM solution of octopeptide 4Rh prepared in α-MEM medium. At selected time periods, cells were washed and suspended in sample buffer. Cell surface association (4° C.) and cellular uptake (37° C.) of octopeptide 4Rh were analyzed on a FACScan unit (Beckton-Dickinson) after exclusion of dead cells. To monitor the nuclear localization of octopeptides, CHO cells were exposed to 0.2 μM solution of octopeptide 4Rh prepared in α-MEM. At selected time intervals, samples of cells were washed, and their nuclei isolated by following a modified protocol of a method originally described elsewhere (Blobel and Potter, 1966). Briefly, 2×$10^6$ cells were suspended in 1 ml of TKM buffer (5 mM Tris-HCl, 2.5 mM KCl, 5 mM $MgCl_2$, pH 7.5) containing 0.25M sucrose and 0.2% Triton-X100. The cells were placed in a glass-teflon tissue homogenizer and disrupted as a result of 15 strokes with a teflon plunger rotating at 1,700 rpm. The cell lysate was centrifuged at 1000 g for 10 minutes and the supernatant was discarded. The pellet was resuspended in 1 mL of 0.25M sucrose in TKM buffer followed by the addition of 2 mLs of 2.3M sucrose in TKM buffer to bring the final sucrose concentration to 1.6M. The resulting homogenate (3 mLs) was layered on top of 1.5 mLs of 2.3M sucrose in TKM buffer. The sample was centrifuged at 36,000 g for 30 minutes. The resulting pellet containing an enriched preparation of nuclei with no remaining intact cells (as confirmed by microscopy). The fluorescent DNA intercalator, 7-amino actinomycin D (7-AAD; 20 μg/ml; Gill et al., 1975; Zelenin et al., 1984; Rabinovitch et al., 1986) was used to label nuclei just prior to flow cytometry. Staining of isolated nuclei was confirmed by fluorescence microscopy.

Variations of this basic concept lead to the design of a multitude of octopeptides The potential of the octopeptide design is best exemplified by considering a few possible variations of the octopeptide with distinct targeting properties. Octopeptides breast-2 and 3 are examples of cytotoxic octopeptides with the potential to target in vivo classes of breast tumor cells. The cytotoxic component can take the form of an analogue of cisplatin (octopeptide breast-2) or an acridine analogue (octopeptide breast-3), for example. The cytotoxic agent is delivered to the nucleus of cells using the approach outlined for octopeptide 5. The domain that enables these octopeptides to target breast cancer cells is abbreviated PHMFGPTSS (SEQ ID NO: 3). The abbreviation stands for a small peptide of 9 amino acids in length that binds specifically to a human milk fat globule protein tumor-specific site. This peptide was derived from a random search through peptide libraries for a peptide able to bind to a deglycosylated region of HMFG protein present in breast cancer cells. In the case of octopeptide breast-2, the PHMFGPTSS (SEQ ID NO:3) and the NLS domains were introduced as single copies in the C-terminal region ($D^5$ and $D^4$ domains respectively) in comparison to octopeptide breast-3. These two related octopeptides outline the potential of moving domains inside the octopeptide design, and thus, highlight the flexiblility of the synthetic strategy.

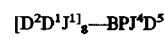

where
  $D^1$ is CTS (SEQ ID NO:2)
  $J^1$ is Gly-Gly
  $D^2$ is Cisplatin
  BP is $(Lys)_4(Lys)_2Lys$
  $D^4$ is NLS (SEQ ID NO:1)
  $D^5$ is PHMFGPTSS ( SEQ ID NO: 3).

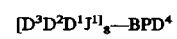

where
  $D^1$ is CTS
  $D^2$ is NLS
  $D^3$ is ACr
  $J^1$ is Gly-Gly
  BP is $(Lys)_4(Lys)_2Lys$
  $D^4$ is PHMFGPTSS. (SEQ ID NO:3)

In summary, the invention provides a flexible arrangement of peptide-based sequences coding for cellular uptake and, in the cases of the embodiments described, nuclear localization signals. Accordingly, the diagnostic and clinical utility of the invention is apparent. The synthetic strategy of the invention establishes an important milestone that will lead to the generation of new classes of intracellular agents able to evaluate or challenge the present knowledge of cellular transport events. More importantly, the use of such de novo peptides should provide important insights in the development of intracellular delivery vectors able to target peptides to appropriate organelles (e.g., endosomes, endoplasmic reticulum) during antigen presentation (Barber and Parham, 1993; Jackson and Peterson, 1993), to localize antisense oligonucleotides to the nucleus of cells (Stein and Cheng, 1993) and to reroute drugs designed to block signalling pathways or to alter DNA replication, into defined cellular compartments (Brugge, 1993; Laduron, 1994).

The introduction of binding domains inside N-terminal branches will improve the avidity of the resulting peptide conjugate for efficiently binding to cell surfaces and intracellular receptors while the introduction of such domains in single copies in the C-terminal arm lowers the overall mass and complexity of the peptide conjugate, features that would influence the immunogenicity, biological clearance rates and synthetic complexity of the peptide conjugate.

From the foregoing description and examples, the skilled person will appreciate that the invention is of a broader scope than the specific octopeptides illustrated. A significant strength of the invention is its versatility and wide applicability.

REFERENCES

Arnold, L. J. Jr., Dagan, A. Gutheil, J., and Kaplan, N. O. (1979). Antineoplastic activity of poly(L-lysine) with some ascites tumour cells. Proc. Natl. Acad. Sci. U.S.A. 76, 3246–3250.

Barber, L. D., and Parham, P. (1993). Peptide binding to major histocompatibility complex molecules. Annu. Rev. Cell Biol. 9, 163–206.

Blobel, G., and Potter, V. R. (1966). Nuclei from rat liver: isolation method that combines purity with high yield. Science 154, 1662–1665.

Breeuwer, M., and Goldfarb, D. S. (1990). Facilitated nuclear transport of histone H1 and other small nucleophilic proteins. Cell 60, 999–1008.

Brinkmann, U., Buchner, J., and Pastan, I. (1992). Independent domain folding of pseudomonas exotoxin and single-chain immunotoxins:influence of interdomain connections. Proc. Natl. Acad. Sci. U.S.A. 89, 3075–3079.

Brugge, J. S. (1993). New intracellular targets for therapeutic drug design. Science 260, 918–919.

Chaudhary, V. K., FitzGerald, D. J., Adhya, S., and Pastan, I. (1987). Activity of a recombinant fusion protein between transforming growth factor type α and Pseudomonas toxin. Proc. Natl. Acad. Sci. U.S.A. 84, 4538–4542.

Chaudhary, V. K., Mizukami, T., Fuerst, T. R., FitzGerald, D. J., Moss, B., Pastan, I., and Berger, E. A. (1988). Selective killing of HIV-infected cells by recombinant human CD4-Pseudomonas exotoxin hybrid protein. Nature 335, 369–372.

Dworetzky, S. I., Lanford, R. E., and Feldherr, C. M. (1988). The effects of variations in the number and sequence of targeting signals on nuclear uptake. J. Cell Biol. 107, 1279–1287.

Ehrenberg, B., Montana, V., Wei, M.-D., Wuskell, J. P., and Loew, L. M. (1988). Membrane potential can be determined in individual cells from the nernstian distribution of cationic dyes. Biophys. J. 53, 785–794.

Farkas, D. L., Wei, M.-D., Febbroriello, P., Carson, J. H., and Loew, L. M. (1989). Simultaneous imaging of cell and mitochondrial membrane potentials. Biophys. J. 56, 1053–1069.

Field, G. B., and Noble, R. L. (1990). Solid-phase peptide synthesis utilizing 9-fluoromethoxycarbonyl amino acids. Int. J. Peptide Protein Res. 35, 161–214.

Gill, J. E., Jotz, M. M., Young, S. G., Modest, E. J., and Sengupta, S. K. (1975). 7-amino-actinomycin D as a cytochemical probe. I. Spectral properties. J. Histochem. Cytochem. 23, 793–799.

Goldfarb, D., Gariepy, J., Schoolnik, G., and Kornberg, R. D. (1986). Synthetic peptides as nuclear localization signals. Nature 322, 641–644.

Jackson, M. R., and Peterson, P. A. (1993). Assembly and intracellular transport of MHC class I molecules. Annu. Rev. Cell Biol. 9, 207–235.

Jans, D. A., Ackermann, M. J., Bischoff, J. R., Beach, D. H., and Peters, R. (1991). p34cdc2-mediated phosphorylation at T124 inhibits nuclear import of SV-40 T antigen proteins. J. Cell Biol. 115, 1203–1212.

Kalderon, D., Richardson, W. D., Markham, A. F., and Smith, A. E. (1984). Sequence requirements for nuclear localization of simian virus 40 large-T antigen. Nature 311, 33–38.

Kreitman, R. J., Hansen, H. J., Jones, A. L., FitzGerald, D. J., Goldenberg, D. M., and Pastan, I. (1993). Pseudomonas exotoxin-based immunotoxins containing the antibody LL2 and LL2-Fab' induce regression of subcutaneous human B-cell lymphoma in mice. Cancer Res. 53, 819–825.

Laduron, P. M. (1994). From receptor internalization to nuclear translocation:New targets for long-term pharmacology. Biochem. Pharmacol. 47, 3–13.

Lanford, R. E., Kanda, P., and Kennedy, R. C. (1986). Induction of nuclear transport with a synthetic peptide homologous to the SV40 T antigen transport signal. Cell 46, 575–582.

Leonetti, J. P., Degols, G., and Lebleu, B. (1990). Biological activity of oligonucleotide-poly(L-lysine) conjugates: mechanism of cell uptake. Bioconj. Chem. 1, 149–153.

Lorberboum-Galski, H., FitzGerald, D., Chaudhary, V., Adhya, S., and Pastan, I. (1988). Cytotoxic activity of an interleukin 2-Pseudomonas exotoxin chimeric protein produced in Escherichia coli. Proc. Natl. Acad. Sci. U.S.A. 85, 1922–1926.

Moll, T., Tebb, G., Surana, U., Robitsch, H., and Nasmyth, K. (1991). The role of phosphorylation and the CDC28 protein kinase in cell cycle-regulated nuclear import of the S. cerevisiae transcription factor SW15. Cell 66, 743–758.

Mosmann, T. (1983). Rapid colorimetric assay for cellular growth and survival:application to proliferation and cytotoxicity assays. J. Immun. Methods 65, 55–63.

Newmeyer, D. D., and Forbes, D. J. (1988). Nuclear import can be separated into distinct steps in vitro:nuclear pore binding and translocation. Cell 52, 641–653.

Rabinovitch, P. S., Torres, R. M., and Engel, D. (1986). Simultaneous cell cycle analysis and two-color surface immunofluorescence using 7-amino actinomycin D and single laser excitation:applications to study of cell activation and the cell cycle of murine LY-1 B cells. J. Immunol. 136, 2769–2775.

Richardson, W. D., Mills, A. D., Dilworth, S. M., Laskey, R. A., and Dingwall, C. (1988). Nuclear protein migration involves two steps:rapid binding at the nuclear envelope followed by slower translocation through nuclear pores. Cell 52, 655–664.

Roberts, B. L., Richardson, W. D., and Smith, A. E. (1987). The effect of protein context on nuclear location signal function. Cell 50, 465–475.

Ryser, H. J.-P., and Shen, W. C. (1978). Conjugation of methotrexate to poly(L-lysine) increase drug transport and overcome drug resistance in cultured cells. Proc. Natl. Acad. Sci. U.S.A. 75, 3867–3870.

Ryser, H. J.-P., Mandel, R., Hacobian, A., and Shen, W.-C. (1988). Methotrexate-poly(lysine) as a selective agent for mutants of Chinese hamster ovary cells defective in endocytosis. J. Cell. Physiol. 135, 277–284.

Shen, W. -C., and Ryser, H. J.-P. (1978). Conjugation of poly-L-lysine to albumin and horseradish peroxidase:a novel method of enhancing the cellular uptake of proteins. Proc. Natl. Acad. Sci. U.S.A. 75, 1872–1876.

Shen, W. C., and Ryser, H.J.-P. (1979). Poly(L-lysine) and poly(D-lysine) conjugates of methotrexate:different inhibitory effect on drug resistant cells. Mol. Pharmacol. 16, 614–622.

Siegall, C. B., Chaudhary, V. K., FitzGerald, D. J., and Pastan, I. (1988). Cytotoxic activity of an interleukin 6-Pseudomonas exotoxin fusion protein on human myeloma cells. Proc. Natl. Acad. Sci. U.S.A. 85, 9738–9742.

Stanners, C. P., Elicieri, G., and Green, H. (1971). Two types of ribosomes in mouse-hamster hybrid cells. Nature New Biol. 230, 52–54.

Stein, C. A., and Cheng, Y. -C. (1993). Antisense oligonucleotides as therapeutic agents. Is the bullet really magic? Science 261, 1004–1011.

Tam, J. P. (1988). Synthetic peptide vaccine design: synthesis and properties of a high-density multiple antigenic peptide system. Proc. Natl. Acad. Sci. U.S.A. 85, 5409–5413.

Tam, J. P. (1989). High-density multiple antigen-peptide system for preparation of antipeptide antibodies. Methods Enzymol. 168, 7–15.

Tam, J. P., and Lu, Y -A. (1989). Vaccine engineering: enhancement of immunogenicity of synthetic peptide vaccines related to hepatitis in chemically defined models consisting of T- and B-cell epitopes. Proc. Natl. Acad. Sci. U.S.A. 86, 9084–9088.

Vogel, B. E., Lee, S. -J., Hildebrand, A., Craig. W., Pierschbacher, M. D., Wong-Staal, F., and Ruoslahti, E. (1993). A novel integrin specificity exemplified by binding of the $\alpha_v\beta_5$ integrin to the basic domain of the HIV Tat protein and vitronectin. J. Cell Biol. 121, 461–468.

Zelenin, A. V., Poletaev, A. I., Stepanova, N. G., Barsky, V. E., Kolesnikov, V. A., Nikitin, S. M., Zhuze, A. L., and Gnutchev, N. V. (1984). 7-amino-actinomycin D as a specific fluorophore for DNA content analysis by laser flow cytometry. Cytometry 5, 348–354.

I claim:

1. A branched synthetic peptide conjugate intracellular vehicle having the formula I:

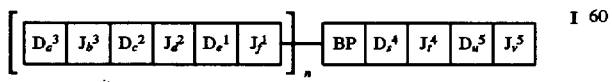

where D is a domain which is a peptide or peptide mimic specific for binding to a target cell surface receptor, or for enabling the transport of the branched synthetic peptide conjugate across the plasma membrane of a cell, or for localization into a specific internal cell compartment; a cytotoxic group; or a diagnostic probe;

J is linear and may be a junctional segment or spacer that may have a chemically active moiety or a marker, a carboxy-terminal structural unit which is an amino acid residue, or a short peptide;

BP is a branched polymer comprising diaminocarboxylic acid residues which provide the branched synthetic peptide conjugate with a plurality of amino-terminal portions;

where each of a, b, c, d, e, f, s, t, u, or v may be 0 or 1; and at least two of a, c, e, s and u is 1;

n is an integer ≧2; and under physiological conditions one of $D^1$, $D^2$ or $D^3$ is present and is a polycationic linear peptide or peptide mimic which enables the transport of the branched synthetic peptide conjugate across the plasma membrane of a cell.

2. A branched synthetic peptide conjugate as claimed in claim 1, wherein at least one D which is present is CTS (SEQ ID NO:2), NLS (SEQ ID NO:1), acridine, a metal chelator, PHMFGPTSS (SEQ ID NO:3) or cisplatin.

3. A branched synthetic peptide conjugate as claimed in claim 1, wherein BP is $(Lys)_4(Lys)_2Lys$ providing eight amino-terminal sites.

4. A branched synthetic peptide conjugate as claimed in claim 1 having a carboxy-terminal residue, wherein the carboxy-terminal residue is βAla.

5. A branched synthetic peptide conjugate as claimed in claim 1, wherein a $J^4$ or $J^5$ carboxy-terminal structural unit is present which is Tyr-Gly-βAla.

6. A branched synthetic peptide conjugate as claimed in claim 1, wherein f is 1.

7. A branched synthetic peptide conjugate as claimed in claim 1, wherein no two D's which are present are the same.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 12 amino acids
( B ) TYPE: amino acid
( C ) STRANDEDNESS: single stranded
( D ) TOPOLOGY: linear ( x i ) SEQUENCE DESCRIPTION: SEQ ID NO:1:

Thr Pro Pro Lys Lys Lys Arg Lys Val Glu Asp Pro
                  5                          10

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single stranded
( D ) TOPOLOGY: linear ( x i ) SEQUENCE DESCRIPTION: SEQ ID NO:2:

Lys Lys Lys Lys Lys
              5

( 2 ) INFORMATION FOR SEQ ID NO:3:

( i ) SEQUENCE CHARACTERISTICS:
( A ) LENGTH: 9 amino acids
( B ) TYPE: amino acid
( C ) STRANDEDNESS: single stranded
( D ) TOPOLOGY: linear ( x i ) SEQUENCE DESCRIPTION: SEQ ID NO:3:

Pro His Met Phe Gly Pro Thr Ser Ser
              5